(12) United States Patent
Katznelson et al.

(10) Patent No.: US 6,490,473 B1
(45) Date of Patent: Dec. 3, 2002

(54) SYSTEM AND METHOD OF INTERACTIVE POSITIONING

(75) Inventors: Ehud Katznelson, Ramat-Yishai; Moran Shochat, Kibbutz Dalia; Varda Gottfried, Haifa; Zvi Polunsky, Holon; Elyakim Bosak, Zichron Yaacov, all of (IL)

(73) Assignee: Coin Medical Technologies, Ltd., Yokneam Elit (IL)

( * ) Notice: Subject to any disclaimer, the term of this patent is extended or adjusted under 35 U.S.C. 154(b) by 0 days.

(21) Appl. No.: 09/545,383

(22) Filed: Apr. 7, 2000

(51) Int. Cl.$^7$ ................................................ A61B 5/00
(52) U.S. Cl. ........................ 600/410; 606/130; 600/411; 600/414
(58) Field of Search ................................. 600/407, 427, 600/429, 426, 410, 411, 414, 417, 415; 324/307, 909, 318, 322; 378/206, 197, 205, 20; 356/375, 152.3, 152.1, 141.1, 141.2, 152.2; 606/130

(56) References Cited

U.S. PATENT DOCUMENTS

| 5,682,890 | A | * | 11/1997 | Kormos et al. | 600/417 |
|---|---|---|---|---|---|
| 5,769,861 | A | * | 6/1998 | Vilsmeier | 606/130 |
| 5,772,594 | A | * | 6/1998 | Barrick | 600/407 |
| 6,026,315 | A | * | 2/2000 | Lenz et al. | 600/414 |
| 6,050,724 | A | * | 4/2000 | Schmitz et al. | 378/205 |
| 6,120,180 | A | * | 9/2000 | Graumann | 378/206 |
| 6,139,183 | A | * | 10/2000 | Graumann | 378/206 |
| 6,149,592 | A | * | 11/2000 | Yanof et al. | 600/427 |
| 6,161,033 | A | * | 12/2000 | Kuhn | 600/419 |
| 6,216,029 | B1 | * | 4/2001 | Paltieli | 600/411 |

* cited by examiner

Primary Examiner—Marvin M. Lateef
Assistant Examiner—Eleni Mantis Mercader
(74) Attorney, Agent, or Firm—Pennie & Edmonds LLP

(57) ABSTRACT

A positioning system for determining the relation between a coordinate set of a scanning apparatus such as an MRI and a coordinate set of a tracking system so as to allow determining the position of a selected target on an image of a patient acquired by the scanning apparatus in the coordinate set of the tracking apparatus and vice versa. The system comprises reference points positioned in predetermined location relative to the coordinate set of the scanning apparatus; tracking system adapted to detect and determine the position of the reference points, relative to the coordinate set of the tracking system; processing device adapted to communicate with the tracking system and adapted to determine the relation between the coordinate set of the scanning apparatus and the coordinate set of the tracking system, translating the coordinates of the target on the image acquired by the scanning apparatus to corresponding coordinates on the coordinate set of the tracking system.

14 Claims, 5 Drawing Sheets

SYSTEM AND METHOD OF INTERACTIVE POSITIONING

FIELD OF THE INVENTION

The present invention relates to medical scanning. More particularly the present invention relates to a method and apparatus of interactive positioning by registration and alignment of a medical scanner's image coordinate set with the physical coordinate set so as to facilitate accurate positioning during medical scanning and/or surgical procedure.

BACKGROUND OF THE INVENTION

When performing medical scanning procedure, precision in localization of different objects or areas within the patient's tissue is of crucial importance. This is especially true for surgical procedures performed in a closed body area, when visualization of the target is impossible (i.e. within the patient's head, stomach etc.). One example is brain surgery, where knowledge of the exact localization of various anatomies allows planning of the procedure and avoiding unnecessary damage to healthy surrounding tissue. Recent diagnostic methods such as computerized tomography (CT), magnetic resonance imaging (MRI), positron emission tomography (PET), nuclear medical apparatus and other medical scanning methods allow accurate pre-operative diagnosis. Nevertheless, these pre-operative pictures are of limited relevance once a surgical procedure is performed since they depend on the coordinates of the patient which might change during the course of operation due to different positioning or on brain shift during surgery.

To overcome this problem, stereotactic surgery and navigation are commonly used and are based on pre-operative images and on rigid markers fixed to the patient. Still, registration of the patient is always needed to compare pre-operative scans and the current situation during surgery. Moreover, any changes occurring during surgery are not accounted for.

Registration of the patient as a reference for determining the position of surgical instruments or probes is known.

In U.S. Pat. No. 5,782,765 (Jonkman), titled MEDICAL POSITIONING SYSTEM, filed in 1996, and incorporated herein by reference, there was disclosed a method and apparatus for positioning a probe inside a patient including a plurality of transmitter/receiver nodes arranged around the patient for communicating with the probe and generating navigation signals, a system for generating one or more positional signals in response to the navigational signals, and a system for collecting and analyzing those positional signals to determine the location of the medical instrument inside the patient's body. The transmitting/receiving nodes may be arranged on a flexible blanket which is wrapped around and adhered to the patient's body or over a table supporting the patient's body.

U.S. Pat. No. 5,871,455 (Bucholz), titled SYSTEM FOR INDICATING THE POSITION OF A SURGICAL PROBE WITHIN A HEAD ON AN IMAGE OF THE HEAD, filed in 1995, suggested a similar approach. There was disclosed a system for determining a position of a probe relative to an object such as a head of a body of a patient. The head includes a surface such as a forehead having a contour. Cross sectional images of the head are scanned and stored as a function of the forehead contour. If the forehead contour does not appear in the scan images, then the position of the forehead contour relative to the scan images is determined with an optical scanner and a ring. During surgery, the optical scanner also determines the position of the forehead relative to the ring. An array for receiving radiation emitted from the probe and from the ring generates signals indicating the position of the tip of the probe relative to the ring. A stereotactic imaging system generates and displays an image of the head corresponding to the measured position of the tip of the probe. The system may also display scan images from different scanning technologies which scan images correspond to the same position in the head (See also U.S. Pat. No. 5,383,454).

It is a main object of the present invention to facilitate the registration of the coordinate set of the scanner to establish the relation to an additional independent coordinate set. This way a definite relation between the two coordinate sets may be established, allowing positioning and location of a certain point in one coordinate set in the other set of coordinates and vice versa.

It is a purpose of the present invention to provide a positioning system and method that refers the coordinate set of the imaging device itself, for example the image coordinate set in an MRI apparatus, by registering the magnet assembly or any other stationary object or object of known location with or in the immediate vicinity of the scanner's scanned region.

It is yet another object of the invention to provide such method and system for positioning that is independent of the patient's position within the scanned region.

Another object of the present invention is to provide a positioning method and system that is based on registering the spatial coordinates of the scanner thus allowing the relation of the images obtained after the registration to the exact position of the scanned object. Alternatively, any change in the position of the scanner can be measured as well and related to the coordinates of the object of interest within the image.

BRIEF DESCRIPTION OF THE INVENTION

A positioning method comprising spatial registration of reference points of known location on an imager in order to perform a highly accurate procedure based on images acquired by the imager. The images are acquired and stored as a function of the position of the patient within the scanner. Moreover, every point within the imaging volume is determinable. The relation between the coordinate set of the scanner and the real physical coordinates is established by registration of several reference points of known location on the scanner, forming a reference space. The center of this registered space and the orientation of the coordinate system of the reference space are known with respect to the center and the direction of the coordinate set of the images acquired by the same imager. Thus the coordinate set of the image has a fixed position in space and can be used to position an object relative to images acquired by the scanner. In another embodiment of the present invention the registration is performed using an array of receiving/emitting/reflecting sources attached to a probe. An adjacent emitting/receiving detection device, whose position and orientation is known in relation to the scanner, is used to obtain the signals determining the coordinates of the scanner.

There is thus provided, in accordance with a preferred embodiment of the present invention, a positioning system for determining the relation between a coordinate set of a scanning apparatus and a coordinate set of a tracking system so as to allow determining the position of a selected target on an image of a patient acquired by the scanning apparatus in the coordinate set of the tracking apparatus and vice versa, the system comprising:

reference points means positioned in predetermined location relative to the coordinate set of the scanning apparatus;

tracking means adapted to detect and determine the position of said reference points means, relative to the coordinate set of the tracking means;

processing means adapted to communicate with said tracking means and adapted to determine the relation between the coordinate set of the scanning apparatus and the coordinate set of the tracking means, and adapted to translate the coordinates of the target on the image acquired by the scanning apparatus to corresponding coordinates on the coordinate set of the tracking means.

Furthermore, in accordance with another preferred embodiment of the present invention, said reference points means comprise markers detectable by said tracking means.

Furthermore, in accordance with another preferred embodiment of the present invention, said tracking means is an optical tracking system.

Furthermore, in accordance with another preferred embodiment of the present invention, said reference points means comprise markers detectable by said tracking means.

Furthermore, in accordance with another preferred embodiment of the present invention, said optical tracking system operates in IR.

Furthermore, in accordance with another preferred embodiment of the present invention, said optical tracking system comprises:

IR transponder adapted to illuminate IR light on said reference points means, and adapted to receive reflected IR light from said reference points means;

analyzing means for analyzing the received reflected IR light digitize it in3D and calculate the position of said reference points means.

Furthermore, in accordance with another preferred embodiment of the present invention, said tracking means comprises detecting means for detecting tracking signal the reference points means and analyzing means for analyzing the detected tracking signal and calculating the position of said reference points means.

Furthermore, in accordance with another preferred embodiment of the present invention, said processing means include coordinate transformation software.

Furthermore, in accordance with another preferred embodiment of the present invention, processing means is further adapted to provide spatial guidance so as to enable positioning of the surgical probe on a predetermined physical target location corresponding to a selected target on the image.

Furthermore, in accordance with another preferred embodiment of the present invention, there is provided a positioning method for determining the relation between a coordinate set of a scanning apparatus and a coordinate set of a tracking system so as to allow determining the position of a selected target on an image of a patient acquired by the scanning apparatus in the coordinate set of the tracking apparatus and vice versa, the method comprising the steps of:

a. providing reference points means positioned in predetermined location relative to a predetermined coordinate set of the scanning apparatus;

b. providing tracking means adapted to detect and determine the position of said reference points means, relative to the coordinate set of the tracking means;

c. providing processing means adapted to communicate with said tracking means and adapted to determine the relation between the coordinate set of the scanning apparatus and the coordinate set of the tracking means, and adapted to translate the coordinates of the target on the image acquired by the scanning apparatus to corresponding coordinates on the coordinate set of the tracking means;

d. determining the position of the reference points means relative to the coordinate set of the tracking means;

e. calculating the position of the reference points means with respect to the coordinate set of the scanning apparatus and determining the transformation matrix between the coordinate set of the tracking means and the scanning apparatus coordinate set; and f. selecting a target on the image and transforming its position to the coordinate set of the tracking means using the transformation matrix;

Furthermore, in accordance with another preferred embodiment of the present invention, the transformation matrix is a rotation and/or shift transform matrix.

BRIEF DESCRIPTION OF THE FIGURES

In order to better understand the present invention, and appreciate its practical applications, the following Figures are provided and referenced hereafter. It should be noted that the Figures are given as examples only and in no way limit the scope of the invention as defined in the appending Claims. Like components are denoted by like reference numerals.

DETAILED DESCRIPTION OF THE INVENTION AND FIGURES

Figure 1:
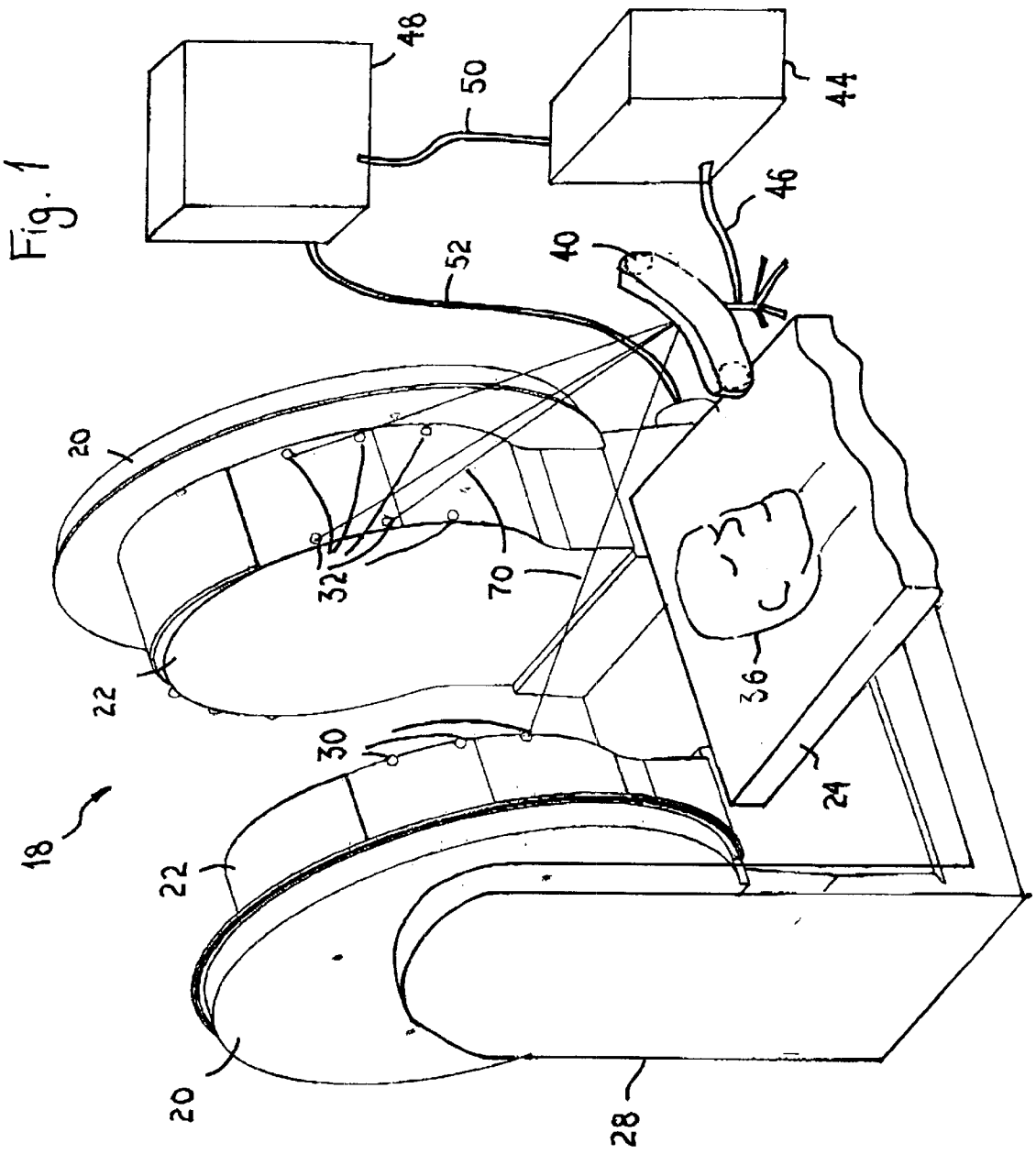
FIG. 1 illustrates a positioning system in accordance with a preferred embodiment of the present invention, with reference points on the magnet assembly of an MRI apparatus.

A main aspect of the present invention is a positioning method and device that registers reference points or area located on the scanner that is used for production of the images. Once the registered reference point form a space of known coordinates, the geomechanical center of the scanner, which may be related to by known transformation to the center of any image acquired, by the scanner, is determined.

Another aspect of the present invention is the provision of a method of controlling the movement of the scanner, and registering its exact coordinates in any given position. The movement of the scanner is, thus, related to the registration of the center of the image.

These registrations allow exact location of any object (or anatomy) within the image. Moreover, any movement of the scanner is accounted for in the exact coordinate system. The exact position of the center of the scanner is always registered and any image acquired by the scanner has known coordinated in space.

The registration is performed using an array of markers positioned in a known relation to the center of the scanner. The markers are used as reference points to be registered by a tracking system and to determine the center of the imager and, consequently, allow coinciding the coordinate set of the imager with the physical coordinate set. The array may comprise transmitting/receiving markers mounted on a rigid rod. These objects may transmit, receive, reflect (or perform any combination of the above) traceable radiation to a tracking device, at a predetermined position relative to the scanner. The radiation transmitted/received/reflected could be of any type, according to the required setup. It may comprise light at any wavelength, sound waves or any different radiation. These markers, mounted on the pointing device (the rod) may be organized in space in different fixed orientations, which will be detected by the tracking device. The pointing device might be an indication probe, setting a trajectory in space or pointing at a specific target. Alternatively, if the imaging is performed during a surgical procedure, the probe might be connected to a surgical device, or a microscope or endoscope or the like. Alternatively, the registration may be performed with reference points positioned on the scanning apparatus itself or on traceable location relative to the scanning apparatus coordinate set. Another alternative would be to use reference points on the patient's bed, provided the position and orientation of the bed is known throughout the procedure (for example, a patient's bed used in superconductor MRI apparatus, where the bed is guided and repositioned within the center of imaging of the apparatus inside the magnet assembly).

Generally, the main aspect of the present invention is the registration of the scanner's coordinate set to an additional independent coordinate set. This way a definite relation between the two coordinate sets may be established, allowing positioning and location of a certain point in one coordinate set in the other set of coordinates and vice versa.

The system and method of the present invention is hereby described with reference to the accompanying drawings. In order to better understand the prospects of the present invention the positioning method and system relate to an MRI apparatus and MRI procedure, however any person skilled in the art could easily implement the present invention on different scanning apparatus, such as CT scanners, positron emission tomography (PET), nuclear medicine apparatus etc. and still remain within the scope of the present invention as defined by the appended Claims.

Throughout this paper the term "scanner" generally relates to any radiological apparatus used for acquiring an image; "tracking system" means any system for identifying the relative position of points and orientations of lines/planes in space; "tracking sensor" means any receiver adapted for receiving signals reflected or generated from a certain point and identify its relative position in a defined space; "marker" means a signal source either passive or active, adapted to reflect (when passive) or emit (when active) traceable signal receivable by a tracking sensor; "pointing device" is a device, usually but not always a rod, provided with a marker or an array of markers on it.

Reference is now made to FIG. 1, illustrating a general view of a positioning system in accordance with the present invention.

An MRI imaging end is shown, comprising a magnet assembly 18 consisting of a pair of magnets 22, with gradient coils 20, held by a U-shaped frame 24—this particular MRI apparatus is an interventional MRI apparatus, such as the one described in U.S. Pat. No. 5,900,793 (Katznelson et al.). The magnet assembly 18 may be repositioned along a vertical axis, using a motion control system, capable of moving frame 24 along arms 28. The motion is achieved by means of a motor or motors not shown in this Figure.

An array of markers (reference points 30 and 32) is provided on the edge surface of both magnets 22. The marker array comprise a predetermined number—in this example 12—of IR (Infra Red) reflecting small surfaces (for example, semispherical), distributed in known positions with respect to the scanners coordinate set (e.g. the origin of the scanner's coordinate axes—the center of axes). By knowing the relative location of these reference points with respect to the scanner's image coordinate set the coordinate set of the reference points can be made to coincide with the scanner's coordinate set.

A tracking system is used to register the reference points as well as pointing devices, if used. Sensors—here an IR transponder set 40 consisting of two IR transponders, adapted to illuminate IR light onto the reflecting points array, and adapted to receive the reflected IR light from the markers, is positioned facing the marker array in a predetermined arrangement and position (known height and relative position). The tracking system itself is not a new. In trials carried out by the inventors, a tracking system called Polaris (manufactured and distributed by Northern Digital Inc.). In order to prevent obstruction to the medical team attending the scanner and/or the patient, the marker array as well as the IR transponder are located on a side of the scanner so as to impose as little distraction as possible to the medical team.

IR transponder set 40 communicates (46) with an analyzer 44 which itself communicates (wire 50) with the scanner's processing unit 48 processing unit 48 is the analyzer and image generator of the MRI apparatus and naturally communicates with the imaging side (i.e. the magnet assembly, the gradient coils, and the RF antenna, not shown in the Figure) of the MRI apparatus.

Analyzer 44 is adapted to receive the signal corresponding to the reflected IR light from the markers that was received by the transponder, digitize the signal (3D digitizer), identify the position of the markers (Rotation and/or shift Transformation is a standard procedure, but other transformation functions can be used) and send this information to the scanner's processing unit 48 (usually a computer) where the coordinate sets of the scanner and the markers are combined and superposed. Note that the center of the registered space (of the markers), as well as the orientation of the coordinates are made to coincides with the center and coordinate set of the images acquired by the same imager. Thus the center of the image has a fixed position in space and can be used to position an object relative to real-time images acquired by the imager.

Figure 2:
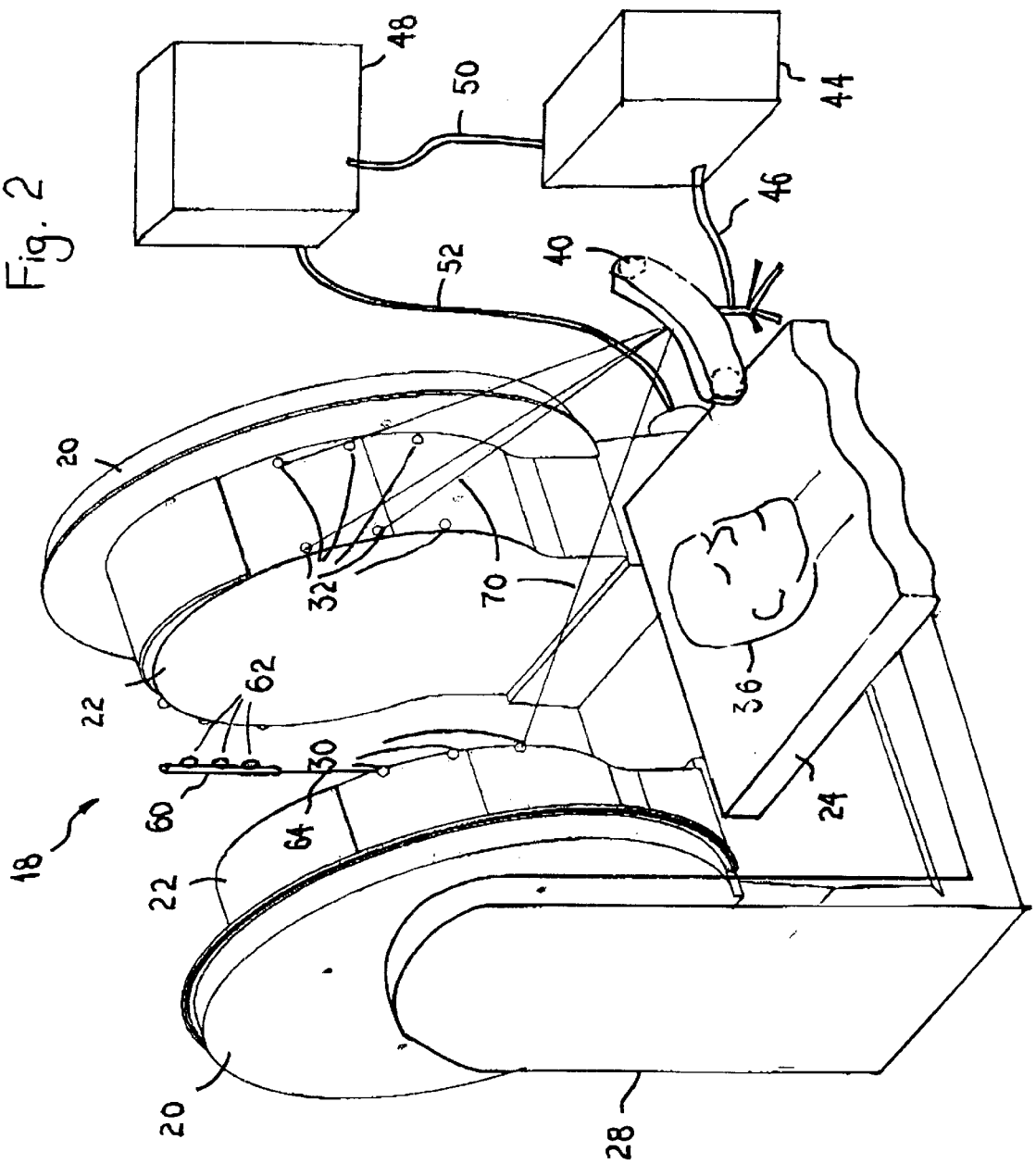
FIG. 2 illustrates a positioning system in accordance with another preferred embodiment of the present invention, using a pointing wand to register the reference points.

It is important to point out that the transponder in the embodiment shown in FIGS. 1 and 2 can be replaced with separate IR light lamp and IR sensor, in which case the IR sensor would replace the IR transponder in an alternative embodiment of the present invention, and the IR lamp would be positioned in a position where it can illuminate IR light on the markers. Furthermore, the method of tracking and registering in itself is not new, and any tracking system can be used. There are tracking systems that employ more than one transponder and/or several sensors and transducers.

The tracking system described herein is an optical system, but other means of tracking and registering can be used, for example ultrasound, sonic system, RF systems, etc., and still be regarded as covered by the scope of the present invention.

FIG. 2 illustrates another preferred embodiment in accordance with the present invention.

In this embodiment the markers 62 are provided on a wand 60, arranged in a prearranged array. At least three markers are provided, aligned along a straight line (in order to allow 3D orientation). The array of markers may be aligned in various geometrical arrangements as long as they are predetermined so as to allow determination of the exact location of the reference points. The wand is attached to a pointing tool 64, which may be a surgical tool, such as a biopsy needle or any other surgical tool, a pointing device, or any other device. In another preferred embodiment, the wand is used on its own, and not attached to any pointing device. The nature of engagement between the wand and the surgical tool is preferably of a temporary kind, so that the wand may be engaged to or disengage from the surgical tool. But it is imperative that once the wand is installed over the tool, the distance between the markers and the distal tip of the tool be known as it is to be accounted for the calculation of the position of the wand, and consequently the target the wand is pointing at.

A predetermined number of reference points (here 12 points, 30 32) is assigned on the scanner (here on the magnet assembly 18).

The tracking system is adapted to identify the location of the markers on the wand. Since the wand is portable, it may serve to register the reference points 30, 32 on the magnet assembly by attaching the distal end of pointing device which the wand is coupled to at its proximal end to the referrice points and register this points. The IR transponder illuminates the markers on the wand, and the analyzer is adapted to determine the location of the reference point by referring to the markers and by taking into account the distance from the closest marker to the distal end of the pointing device (a distance which is predetermined of course). This procedure is repeated for all or at least some reference points (at least three points) so that the coordinate set of the reference points can be determined and superposed by the processing unit 48 on the scanner's image coordinates.

The advantage of the embodiment with the wand is that the wand may serve during the surgery to point desired target locations (such as within the patient's head). The pointing device can be held adjacent the suspected location of the target tissue of the patient 36 (on the operating table 34), and by selecting the target on the image acquired by the MRI apparatus the pointing system can determine whether the surgical tool (or pointing device) is on the right spot or needs to be moved. Furthermore the system may be adapted to provide the exact direction and distance of the pointing device distal tip from the target.

Figure 3:
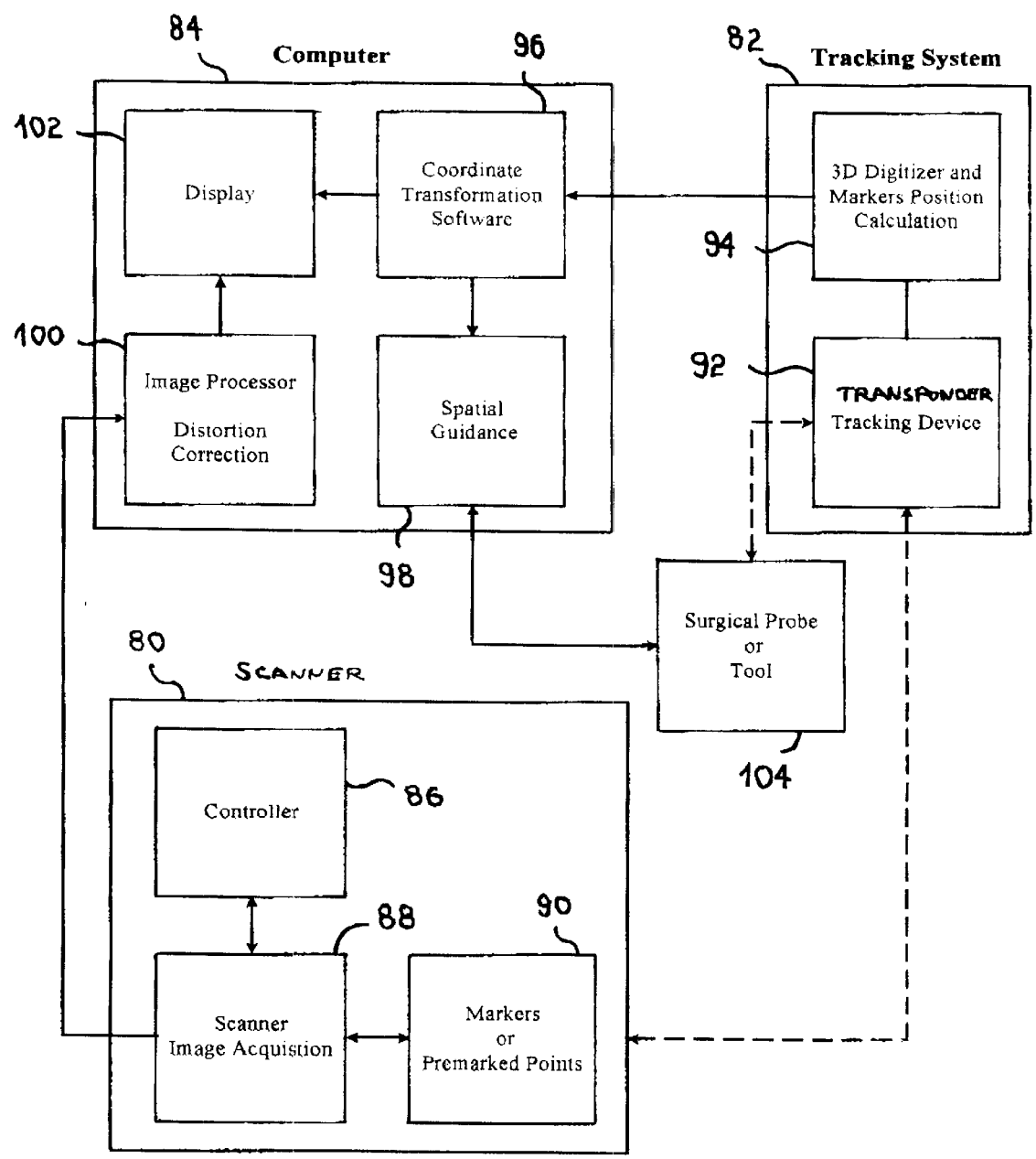
FIG. 3 is a schematic block diagram of the system shown in FIGS. 1 and 2.

FIG. 3 is a schematic block diagram of a pointing system in accordance with the present invention.

FIG. 3 depicts the three main participants: the scanner 80, the tracking system 82 and the interface-a computing unit 84.

The scanner 80 generally comprises a controller 86 which controls the image acquisition. Markers 90 (or premarked reference points—see explanation of FIG. 5) are positioned in known relative locations on the scanner. The markers position is determined by the tracking system 82, by way of detecting the markers by the transponder 92 (as explained earlier), and digitization (3D digitizer 94) and calculation of the markers position. The marker's position is communicated to the computing unit 84.

Computing unit 84 receives image data from the scanner and an image processor 100 processes the image data (optionally performing also distortion correction procedure) and displays the image on a display 102. Coordinate transformation software 96 translates the position of the markers that was transmitted to the computing unit by the tracking system and superposes the coordinates of the markers (i.e. the physical space) on the image coordinates.

This ability to guide the tool is of particular appeal since many times malignant tissue is detectable only on the image but is indistinguishable from healthy tissue in vivo. A surgical probe or tool 104 which is placed in the scanned region may thus be positioned on any desired location on the patient.

The interactive positioning system of the present invention does not use reference points located on the patient (as described in U.S. Pat. No. 5,871,445 or U.S. Pat. No. 5,782,765, for example), but rather uses reference points located on the scanner itself with a definite geometrical relation to the scanner coordinate system. Furthermore, it is anticipated that the magnet assembly 18 be moved up or down in order to be properly aligned with the patients head or organ to be operated on (it is mounted on motor operated positioning arms). In that case, the new position of the magnet assembly can be accurately determined and the new alignment of the coordinate sets can be calculated easily.

The mode of operation of the positioning system and the positioning procedure therein is explained in detail with reference to FIGS. 4 and 5.

Figure 4:
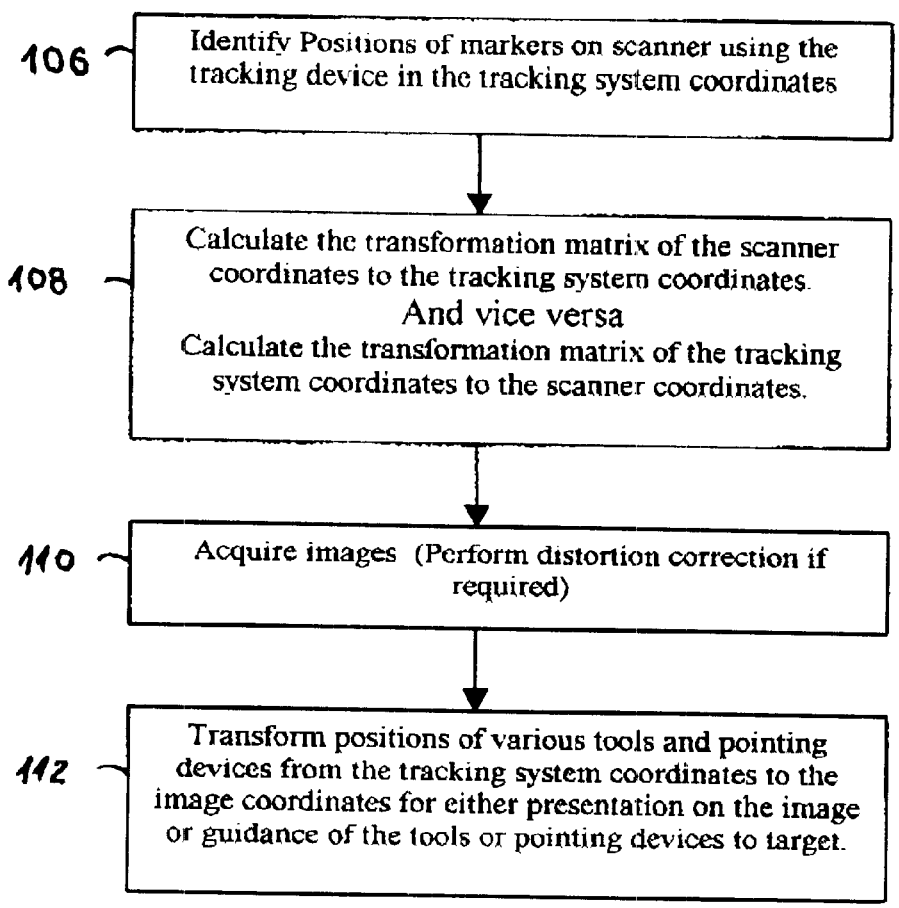
FIG. 4 is a flow chart presenting the steps carried out in a pointing method in accordance with the present invention.

FIG. 4 illustrates a flow chart of the steps carried out in a pointing method in accordance with a preferred embodiment of the present invention, with the system shown in FIG. 1.

First the markers' position is identified 106, then the transformation matrix of the image coordinates to the physical coordinates is determined and vice versa (i.e. the transformation matrix of the physical coordinates to the image coordinates) 108. The image is acquired 110 (performing image distortion correction if necessary) and the position of a surgical tool in the physical coordinates is determined in the image coordinates. The tool is presented on the image or guided to the target location.

Figure 5:
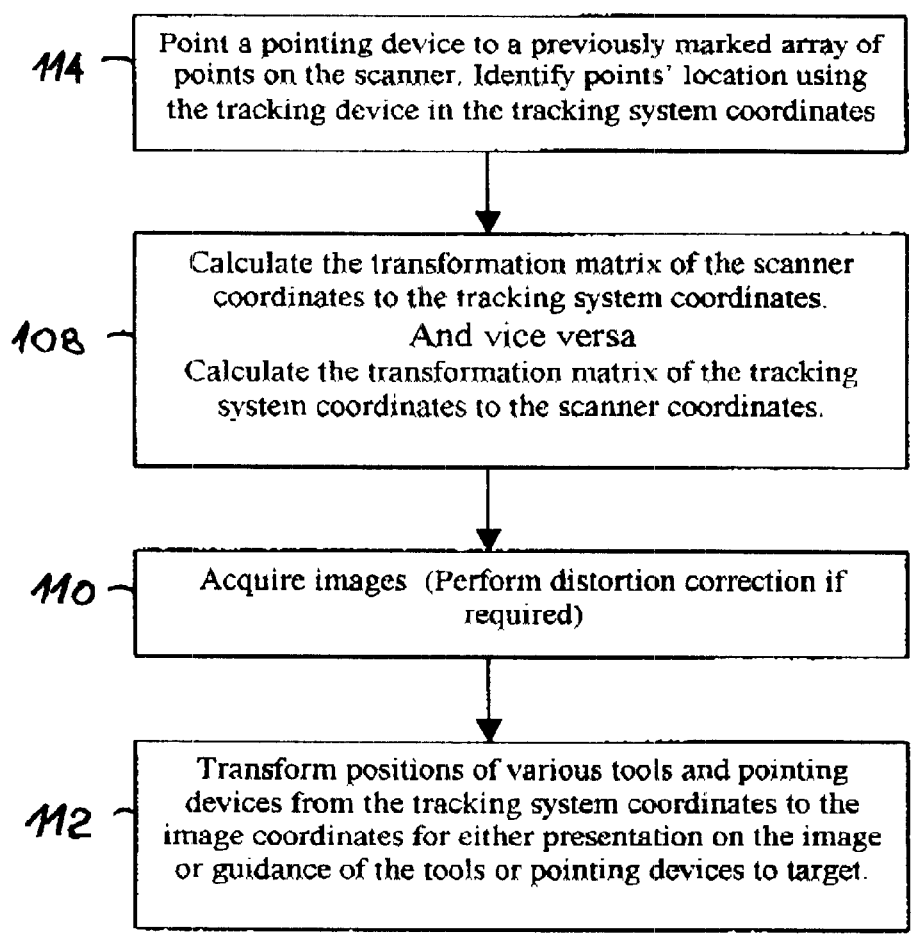
FIG. 5 is a flow chart of the steps carried out in a pointing method in accordance with the present invention.

FIG. 5 is a flow chart of the steps carried out in a pointing method in accordance with the present invention, with the system shown in FIG. 2.

Instead of providing stationary markers as in FIG. 1, reference point 30, 32 (see FIG. 2) are registered separately by placing the wand with the markers with its distal tip on each reference point and registering the position of the wand. By knowing the length of the wand and determining the markers spatial position, the position of the reference point can be determined (simple linear extrapolation). This is repeated for each reference point so that the physical coordinate set is retrieved. The rest of the procedure is similar to the one shown in FIG. 4.

Note that the minimal number of markers (or reference points) for establishing the physical coordinates system is three.

It is important to see that the system and method of the present invention facilitates both determination of the location of a physical target on an image acquired by the scanner, and also the determination of a target on the image in the physical space, thus allowing the medical team to direct a surgical tool to a desired target on the patient by pointing on a target on the image, and vice versa.

It is noted that while the embodiments shown in the accompanying drawings employ IR radiation for the registration of the scanner, this may be performed using any other tracking method, such as employing sound waves for acoustic tracking with acoustic transponder instead of the IR transponder, or employing electromagnetic radiation of various ranges (RF, visible light, microwaves etc.), preferably radiation that is not harmful to the patient or the medical team (IR and sound waves for instance are suitable).

It is understood that the accuracy of the positioning system of the present invention can be made to only be limited to the resolution of the device with the lowest resolution (the MRI apparatus or the optical registration device). Practically, when MRI systems are considered, the accuracy of the pointing system can be refined to the order of one or two pixels).

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

What is claimed is:

1. An MRI positioning system for determining the relation between a coordinate set of a magnetic resonance imaging (MRI) apparatus and a coordinate set of a tracking system so as to allow determining the position of a selected target on an image of a patient acquired by the MRI apparatus in the coordinate set of the tracking apparatus and vice versa, the system comprising:
   reference points means for positioning in predetermined location relative to the coordinate set of the MRI apparatus;
   tracking means for detecting and determining the position of said reference points means, relative to the coordinate set of the tracking means; and
   processing means communicating with said tracking means and determining the relation between the coordinate set of the MRI apparatus and the coordinate set of the tracking means, and translating the coordinates of the target on the image acquired by the MRI apparatus to corresponding coordinates on the coordinate set of the tracking means;
wherein said reference points means are not positioned on the patient.

2. The MRI positioning system according to claim 1, wherein said reference points means comprise markers detectable by said tracking means.

3. The MRI positioning system according to claim 1, wherein said tracking means is an optical tracking system.

4. The MRI positioning system according to claim 1, wherein said optical tracking system operates in the IR range.

5. The MRI positioning system according to claim 1, wherein said optical tracking system comprises:
   IR transponder for illuminating IR light on said reference points means, and receiving reflected IR light from said reference points means;
   analyzing means for analyzing the received reflected IR light digitize it in 3D and calculate the position of said reference points means.

6. The MRI positioning system according to claim 1, wherein said tracking means comprises detecting means for detecting tracking signal received from the reference points means and analyzing means for analyzing the detected tracking signal and calculating the position of said reference points means.

7. The MRI positioning system according to claim 1, wherein said processing means include coordinate transformation software.

8. The MRI positioning system according to claim 1, wherein the processing means is further adapted to provide spatial guidance so as to enable positioning of a surgical probe on a predetermined physical target location corresponding to a selected target on the image.

9. An MRI positioning method for determining the relation between a coordinate set of a magnetic resonance imaging (MRI) apparatus and a coordinate set of a tracking system so as to allow determining the position of a selected target on an image of a patient acquired by the MRI apparatus in the coordinate set of the tracking apparatus and vice versa, the method comprising the steps of:
   a. providing reference points means for positioning in fixed position relative to the coordinate set of the MRI apparatus;
   b. providing tracking means for detecting and determining the position of said reference points means, relative to the coordinate set of the tracking means;
   c. providing processing means communicating with said tracking means and determining the relation between the coordinate set of the MRI apparatus and the coordinate set of the tracking means, and translating the coordinates of the target on the image acquired by the MRI apparatus to corresponding coordinates on the coordinate set of the tracking means;
   d. determining the position of the reference points means relative to the coordinate set of the tracking means;
   e. calculating the position of the reference points means with respect to the coordinate set of the MRI apparatus and determining a transformation matrix between the coordinate set of the tracking means and the MRI apparatus coordinate set; and
   f. selecting a target on the image and transforming its position to the coordinate set of the tracking means using the transformation matrix;
wherein said reference points means are not on the patient.

10. The MRI positioning method according to claim 9, wherein the transformation matrix is a rotation and/or shift Transform matrix.

11. In a magnetic resonance imaging (MRI) apparatus for imaging a patient, the MRI apparatus including a pair of magnets defining therebetween an imaging volume having a three-dimensional MRI coordinate set, the improvement comprising:
   a plurality of reflective markers positioned on the MRI apparatus in predetermined locations along a periphery of the imaging volume;
   a transponder positioned to cooperate with said plurality of reflective markers by sending at least one signal to the reflective markers and detecting a reflection therefrom;
   a tracking analyzer communicating with the transponder and configured to determine relative positions of the reflective markers to thereby form a 3-dimensional tracking analyzer coordinate set; and
   computing means communicating with the tracking analyzer and configured to establish a relation between the MRI coordinate set and the tracking analyzer coordinate set, and translate coordinates of an image acquired by the MRI apparatus to coordinates on the tracking analyzer coordinate set;
wherein said predetermined locations at which the reflective markers are positioned, are not on the patient.

12. The magnetic resonance imaging (MRI) apparatus according to claim 11, wherein the reflective markers reflect infrared light and the transponder is an infrared transponder.

13. In a magnetic resonance imaging (MRI) apparatus for imaging a patient, the MRI apparatus including a pair of magnets defining therebetween an imaging volume having a three-dimensional MRI coordinate set, the improvement comprising:

a wand provided with at least one reflective marker;

a plurality of reference points defined on the MRI apparatus in predetermined locations along a periphery of the imaging volume;

a transponder positioned to cooperate with the at least one reflective marker by sending at least one signal to the reflective marker and detecting a reflection therefrom, when the wand is in contact with one of said plurality of reference points;

a tracking analyzer communicating with the transponder and configured to determine relative positions of the reference points to thereby form a 3-dimensional tracking analyzer coordinate set; and computing means communicating with the tracking analyzer and configured to establish a relation between the MRI coordinate set and the tracking analyzer coordinate set, and translate coordinates of an image acquired by the MRI apparatus to coordinates on the tracking analyzer coordinate set;

wherein said predetermined locations at which said reference points are defined, are not on the patient.

14. The magnetic resonance imaging (MRI) apparatus according to claim 13, wherein the reflective markers reflect infrared light and the transponder is an infrared transponder.

* * * * *

UNITED STATES PATENT AND TRADEMARK OFFICE
CERTIFICATE OF CORRECTION

PATENT NO.    : 6,490,473 B1
DATED         : December 3, 2002
INVENTOR(S)   : Katznelson, Ehud et al.

It is certified that error appears in the above-identified patent and that said Letters Patent is hereby corrected as shown below:

<u>Title page,</u>
Item [73], please change Assignee from:
"Coin Medical Technologies, Ltd.,
Yokenam Elit (IL)" to read:
-- Odin Technologies Ltd.
Kohav Yokneam, Yokneam, Israel --

Signed and Sealed this

Fourteenth Day of October, 2003

JAMES E. ROGAN
*Director of the United States Patent and Trademark Office*